United States Patent [19]

Wilson

[11] 4,370,791
[45] Feb. 1, 1983

[54] METHOD OF FORMING AN ADJUSTABLE PROSTHETIC ELEMENT

[76] Inventor: Michael T. Wilson, 1259 Monument Blvd., Concord, Calif. 94520

[21] Appl. No.: 248,555

[22] Filed: Mar. 27, 1981

Related U.S. Application Data

[62] Division of Ser. No. 11,126, Mar. 19, 1979, Pat. No. 4,283,800.

[51] Int. Cl.³ .............................................. B23P 19/00
[52] U.S. Cl. ...................................... 29/407; 29/423; 29/428; 264/274
[58] Field of Search .................... 3/12.4, 21, 22, 30; 29/407, 423, 428; 264/40.1, 222, 223; 403/97; 264/274

[56] References Cited

U.S. PATENT DOCUMENTS

| 3,351,955 | 11/1967 | Middleton | 3/21 X |
| 3,940,804 | 3/1976 | Benton et al. | 3/30 |
| 4,156,945 | 6/1979 | May | 3/12.4 |
| 4,186,449 | 2/1980 | Horvath | 3/21 X |
| 4,241,878 | 12/1980 | Underwood | 264/274 X |

FOREIGN PATENT DOCUMENTS

| 169251 | 9/1921 | United Kingdom | 403/97 |
| 853235 | 11/1960 | United Kingdom | 403/97 |
| 978586 | 12/1964 | United Kingdom | 3/21 |

*Primary Examiner*—Ervin M. Combs
*Attorney, Agent, or Firm*—Phillips, Moore, Lempio & Finley

[57] ABSTRACT

A prosthetic device which is adjustable in the transverse plane includes a flanged element moldable in a plastic socket and an element having a toothed superior surface. The plastic socket is formed about the flanged element while using the toothed superior surface as a mold surface. A fastener engages the toothed superior surface and this affixes the formed socket to the toothed element. The fastener may be loosened so that incremental rotation of the toothed element relative the socket is permitted.

4 Claims, 5 Drawing Figures

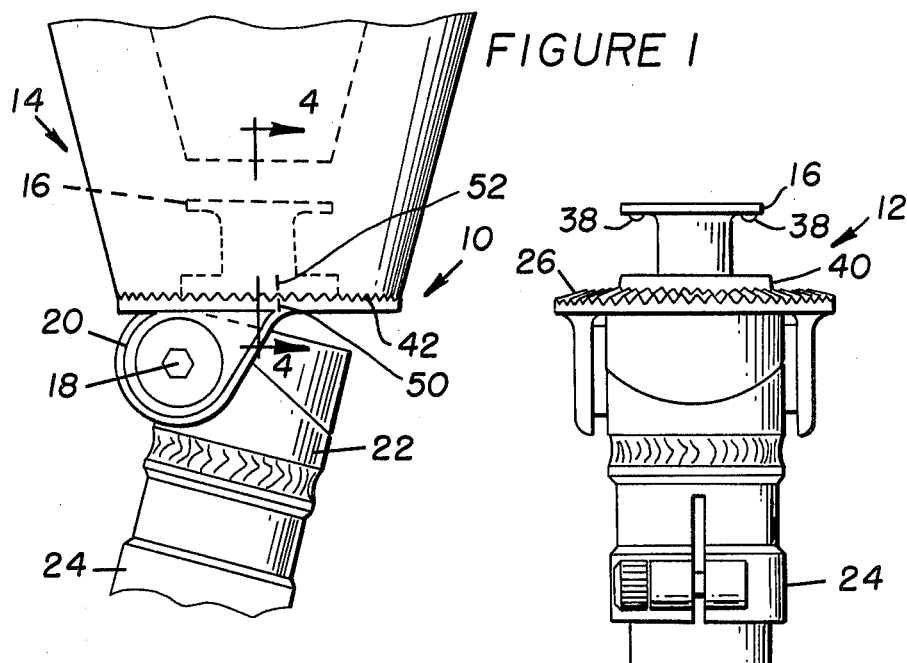
FIGURE 1
FIGURE 2
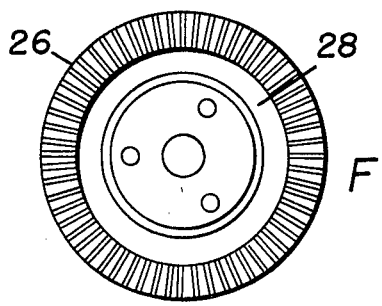
FIGURE 3
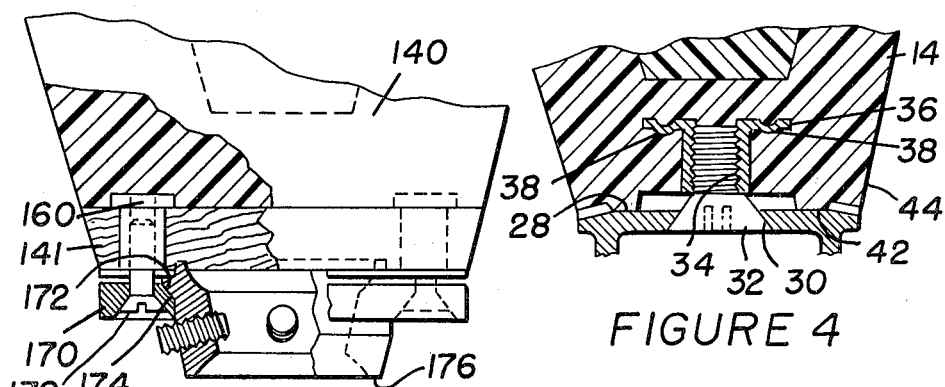
FIGURE 4
FIGURE 5
PRIOR ART

METHOD OF FORMING AN ADJUSTABLE PROSTHETIC ELEMENT

This is a division of Ser. No. 11,126, filed Mar. 19, 1979, Pat. No. 4,283,800.

BACKGROUND OF THE INVENTION

This invention relates to prosthetic devices. In particular it relates to a prosthetic device which may form a portion of a lower limb prosthesis. The device allows incremental rotation in the transverse plane of the inferior portion of the lower limb prosthesis.

In fitting a patient with a prosthesis following amputation of a lower limb, the prosthetist must ensure the prosthesis swings substantially in the sagittal plane during walking by the patient. In particular if the knee is replaced, it is especially important that the knee flex in the sagittal plane as flexion out of the sagittal plane will grossly exaggerate the patient's lameness due to the prosthesis. During initial fitting the prosthetist may build up an artificial limb utilizing adjustable elements as to length and orientation to the patient's body. However the final prosthetic device is best fixed permanently at the various joints thus precluding further adjustment. This may be done by welding, soldering, brazing or the like. Nevertheless, even with the best initial fitting, the patient, while adapting to the artificial limb, may change his stance or gate to the extent that flexion of the knee joint no longer occurs in the sagittal plane. This is particularly difficult to adjust in a permanently bonded artificial limb particularly when the socket, normally molded to fit the patient's residual limb, is fixed to the remaining portion of the prosthesis. Accordingly, adjustable fittings are available to permit separation of the molded socket from the prosthesis and thus permit incremental rotation of the inferior portion of the prosthesis relative the socket. Available devices are usually affixed to the socket by means such as screws or the like. In some instances the fitting is fixed to a wooden member which in turn is molded to the socket. In either case, release of the fitting is accomplished by loosening the various screws so that an externally splined fitting may be rotated relative an internally splined plate which is fixed for screwing to the socket. Although such a device is serviceable and accomplishes the goal, the devices are relatively heavy and do suffer from the drawback of being fixed to the socket in a manner which can result in failure after repeated adjustments. Finally in any prosthetic device it is always appropriate to decrease the weight of any and all elements in order to decrease the strain placed on muscles of the patient. Therefore elimination of any unnecessary parts and the use of lighter materials to replace other parts is particularly appropriate in the design and use of artificial limbs.

SUMMARY OF THE INVENTION

Accordingly, this invention provides an adjustable prosthetic device which includes a prosthetic element adapted on the inferior side for fixture to a second prosthetic element and having formed on the superior side and in the transverse plane a toothed surface. The socket is molded for mating with the toothed surface of the prosthetic element while a flanged element is molded in the socket for use in fixing the socket to the plate. The toothed surface permits incremental rotation in the transverse plane of the socket relative the prosthetic element.

BRIEF DESCRIPTION OF THE DRAWINGS

FIG. 1 is a side elevation view of the adjustable prosthetic device described herein when used as a portion of prosthetic knee joint.

FIG. 2 is a front elevation view of the prosthetic device shown in FIG. 1 before the socket is formed therewith.

FIG. 3 is a plane view of the prosthetic device shown in FIG. 2.

FIG. 4 is a sectional view taken at line 4—4 of FIG. 1 of the prosthetic device shown in FIG. 1.

FIG. 5 is an illustration of a prior art device.

DETAILED DESCRIPTION OF THE PREFERRED EMBODIMENT

Referring to FIG. 1, a prosthesis 10 is shown. Prosthesis 10 includes a prosthetic element 12, (see FIG. 2) a socket 14 and means molded in socket 14 such as flange 16 for fixing socket 14 to prosthetic element 12.

In the embodiment shown, prosthetic element 12 is a knee joint having an axis 18 in the frontal plane such that superior portion 20 and inferior portion 22 may rotate in the sagittal plane relative each other. Inferior portion 22 is formed to receive a second prosthetic element 24 by welding or the like. The structure for fixing second prosthetic element 24 to prosthetic element 12 is set forth in U.S Pat. No. 4,149,280 issued Apr. 17, 1979 to Michael T. Wilson.

Superior portion 20 has formed about the upper or superior side thereof a toothed surface 26 generally formed about the outer perimeter thereof. Toothed surface 26 extends inwardly preferably in an upwardly sloping manner as shown in FIG. 2 approximately 25 percent of the radius of the prosthetic element 12. As can be seen in FIG. 3 prosthetic element 12 is preferably of a circular shape when viewed in a plan view. The toothed surface 26 extends upwardly from the superior portion 20 to form the center depressed area 28 (see FIG. 4). Formed substantially on the center line of the circular superior portion 20 is hole 30 preferably counter sunk on the lower surface as indicated in FIG. 4. Hole 30 is formed to receive a threaded fastening means such as bolt 32 which in the illustration shown in FIG. 4 is flatheaded in the manner of conventional bolts. Looking at FIG. 4 in conjunction with FIG. 1, it can be seen that the configuration of bolt 32 is necessarily flatheaded to permit inferior portion 22 to hinge upwardly meeting superior portion 20 as shown in FIG. 2.

Flange 16 is shown affixed to prosthetic element 12 by bolt 32 in FIG. 4 prior to forming of socket 14. Flange 16 has a centrally formed bore 34 which is threaded to receive bolt 32. The upper or superior surface 36 of flange 16 may be dimpled as at 38 to form a better mating surface with molded socket 14.

A spacer 40 is provided with the prosthetic element 12 for use in forming socket 14. As can be seen in FIG. 4, socket 14 is a molded plastic material which forms the socket of the prosthesis. Since each socket 14 is individually formed for each patient, it is molded at time of assembly to prosthetic element 12 in order to form a mating toothed surface 42. Molding is accomplished in a manner well known in the art and will not be further described here except to state that a mold is formed by the prosthetist to fit the patient's residual limb. In the molding process, flange 16 is fitted as indicated in FIG. 2 with spacer 40 in depressed area 28 by separating the lower portion of flange 16 from superior portion 20. After the plastic formed material of socket 14 is hardened sufficiently to back out bolt 32 from flange 16, thereby separating socket 14 from prosthetic element 12, spacer 40 may be removed. Upon removal of spacer 40, the socket 14 is refitted onto the toothed surface 26 of prosthetic element 12 with the mating toothed surface 42 fitting therein. Bolt 32 may then be tightened in bore 34 of flange 16 thereby affixing socket 14 to prosthetic element 12. It should be noted that upon removal of spacer 40 socket 14 bears against superior portion 28 of toothed surface 26 as indicated above and also in annular fashion at extension 44 of the molded socket as shown in FIG. 4. Spacer 40 has thereupon moved the bearing point outwardly from the axis of bolt 32 while providing a degree of resiliency in the area formed by spacer 40 during the molding process.

It should be noted that spacer 40 is formed with draft as indicated in FIG. 2 so it is easily removable from socket 14 during the forming process. The materials appropriate for spacer 14 include easily machinable plastics such as the nylon group and the acetal homopolymer group, the latter of which includes Delrin manufactured by the E. I. du Pont de Nemours and Company, Inc., Wilmington, Delaware. It should be understood that that other easily machinable plastics could be used with equal ease.

In operation, this prosthesis permits adjustment in the transverse axis of the socket relative to the prosthetic element 12 by the simple expedient of loosening bolt 32 thereby permitting socket 14 to be moved upwardly disengaging toothed surface 42 of socket 14 from toothed surface 26 of prosthetic element 12. Movement of the socket 14 by rotation in the transverse plane may then be accomplished. Thus adjustment of the lower limb is easily performed without separation of the various elements as is required in the prior art device shown in FIG. 5.

In the prior art device shown in FIG. 5, the socket 140 has molded therein a plurality of flange members 160 which are usually also mounted in a lower wooden member 141 affixed to the plastic socket. In this device an annular ring 170 has a splined frusto-conical inner surface 172 which mates with a corresponding splined frusto-conical outer surface 174 formed in a fitting 176 adapted to be affixed to an inferior prosthetic element. Adjustment of this device requires release of the plurality of bolts 178 which threadably engage flange member 160. This particular prior art device is available from the Otto Bock Company of West Germany.

In the invention claimed herein, only a single fastening element 16 is molded in the socket 14 which is to be fastened to the prosthetic element 12 by means of a single screw 32. Adjustment is accomplished by the simple expedient of loosening screw 32 sufficiently to separate the toothed surfaces in order to rotate them either rightwardly or leftwardly as the case may be.

Finally indexing marks 50 and 52 may be used on prosthetic element 12 and socket 14 respectively to orient the two members during removal of spacer 40 and subsequently during adjustment.

Other aspects, objects and advantages of this invention can be obtained from a study of the drawings, the disclosure and the appended claims.

What is claimed is:

1. A method for forming a human prosthesis of at least two elements in which one element is incrementally rotatable in the transverse plane relative a second element, the method comprising the steps of:
   a. providing a first prosthetic element having a toothed superior surface;
   b. providing and securing retention means to said first prosthetic element for removably retaining a molded plastic socket adjacent the first prosthetic element;
   c. providing a removable spacer element between the retention means and the superior surface of the first prosthetic element; and
   d. forming from plastic material, superior to the first prosthetic element, a second prosthetic element in the form of a prosthetic socket about the retention means and said removable spacer element using the toothed superior surface to form the inferior surface of the socket.

2. The method of claim 1 wherein the step of providing retention means includes the steps of:
   providing a flanged bushing having a threaded bore therethrough;
   fixing the flanged bushing to the first prosthetic element proximal the toothed superior surface; and further wherein the method includes the additional step between the aforesaid two steps of;
   providing said spacer element between the flanged bushing and the prosthetic element to orient the bearing surface of the formed socket on the inferior surface of the socket and to provide resiliency to the prosthesis.

3. The method of claim 2 further comprising the steps of
   d. separating the molded plastic socket and the first prosthetic element;
   e. removing the spacer element; and
   f. reassembling the molded plastic socket and the first prosthetic element.

4. The method of claim 3 further comprising a step before the step of separating the molded plastic socket and the first prosthetic element of:
   marking the molded plastic socket and the first prosthetic element with an index mark to facilitate subsequent assembly and adjustment.

* * * * *